(12) United States Patent
Von Der Hardt et al.

(10) Patent No.: US 6,907,770 B2
(45) Date of Patent: Jun. 21, 2005

(54) TEST DEVICE FOR FILTER SYSTEMS

(75) Inventors: Jochen Von Der Hardt, Goettingen (DE); Reinhard Baumfalk, Goettingen (DE); Oscar-Werner Reif, Hannover (DE); Juergen Van Den Boogaard, Coram, NY (US)

(73) Assignee: Sartorius AG, Goettingen (DE)

( * ) Notice: Subject to any disclaimer, the term of this patent is extended or adjusted under 35 U.S.C. 154(b) by 0 days.

(21) Appl. No.: 10/198,074

(22) Filed: Jul. 19, 2002

(65) Prior Publication Data

US 2003/0033856 A1 Feb. 20, 2003

(30) Foreign Application Priority Data

Jul. 19, 2001 (DE) .......................... 101 35 294

(51) Int. Cl.[7] ........................... G01M 3/02; G01M 3/26
(52) U.S. Cl. ................... 73/38; 73/40; 73/407
(58) Field of Search ................ 73/38; 210/741; 224/633; 261/30; 417/298, 313; 62/371, 457.7

(56) References Cited

U.S. PATENT DOCUMENTS

| | | | | |
|---|---|---|---|---|
| 3,392,573 A | * | 7/1968 | Benson et al. ................ 73/38 |
| 3,885,892 A | * | 5/1975 | Dwyer ...................... 417/234 |
| 4,402,214 A | * | 9/1983 | Morgan et al. ............. 73/40.7 |
| 4,449,392 A | * | 5/1984 | Huschke ...................... 73/40 |
| 4,515,007 A | * | 5/1985 | Herman ....................... 73/38 |
| 4,614,109 A | * | 9/1986 | Hofmann ...................... 73/38 |
| 4,662,551 A | * | 5/1987 | Dudley et al. ............. 224/633 |
| 4,701,861 A | * | 10/1987 | Kauke ....................... 700/266 |
| 4,872,974 A | * | 10/1989 | Hirayama et al. ............ 210/90 |
| 4,881,176 A | * | 11/1989 | Kononov .................... 700/271 |
| 5,064,529 A | * | 11/1991 | Hirayama et al. ............ 210/90 |
| 5,282,380 A | * | 2/1994 | DiLeo et al. ................. 73/38 |
| 5,353,630 A | * | 10/1994 | Soda et al. ................... 73/38 |
| 5,417,101 A | * | 5/1995 | Weich ......................... 73/38 |
| 5,457,986 A | * | 10/1995 | DiLeo et al. ................. 73/38 |
| 5,562,427 A | * | 10/1996 | Mangyo et al. ............. 417/313 |
| 5,576,480 A | * | 11/1996 | Hopkins et al. ............... 73/38 |
| 5,594,161 A | * | 1/1997 | Randhahn et al. ............. 73/38 |
| 5,616,828 A | * | 4/1997 | Kuczenski .................... 73/38 |
| 5,674,404 A | * | 10/1997 | Kenley et al. .............. 210/741 |
| 5,808,181 A | * | 9/1998 | Wamsiedler et al. .......... 73/38 |
| 6,021,046 A | * | 2/2000 | McLellan et al. ........... 361/719 |
| 6,055,155 A | * | 4/2000 | von Gutfeld ................ 361/690 |
| 6,171,072 B1 | * | 1/2001 | West et al. ................. 417/298 |
| 6,319,298 B1 | * | 11/2001 | Ng-Gee-Quan .............. 55/331 |
| 6,324,898 B1 | * | 12/2001 | Cote et al. .................... 73/38 |
| 6,360,557 B1 | * | 3/2002 | Reznik ....................... 62/402 |
| 6,527,146 B1 | * | 3/2003 | Tanny et al. ........... 222/189.11 |
| 2001/0037655 A1 | * | 11/2001 | Aarestrup ................. 62/228.4 |
| 2002/0191430 A1 | * | 12/2002 | Meir ......................... 363/141 |
| 2003/0018415 A1 | * | 1/2003 | Sonobe et al. ............. 700/275 |

FOREIGN PATENT DOCUMENTS

| | | | | |
|---|---|---|---|---|
| DE | DD 301119 A | * | 10/1992 | .......... F04B/39/00 |
| GB | 2356939 A | * | 6/2001 | .......... G01N/11/06 |

OTHER PUBLICATIONS

"Filtertester MK2", Carl Prandtl Microfiltration, available on the internet at <http://www.cpm-prandtl.de/english/FiltertesterMK2_eng.htm>.*

* cited by examiner

Primary Examiner—Hezron Williams
Assistant Examiner—David A. Rogers
(74) Attorney, Agent, or Firm—Crowell & Moring LLP

(57) ABSTRACT

A test device (10) for filter systems, including a pneumatic unit (12), a control unit (14) for controlling the pneumatic unit (12), and a data processing unit (16), in which the pneumatic unit (12) is separated from the data processing unit (16) and the control unit (14) by a separating device (18) which substantially shields the pneumatic unit (12) against heat generated in the data processing unit (16) and the control unit (14).

6 Claims, 1 Drawing Sheet

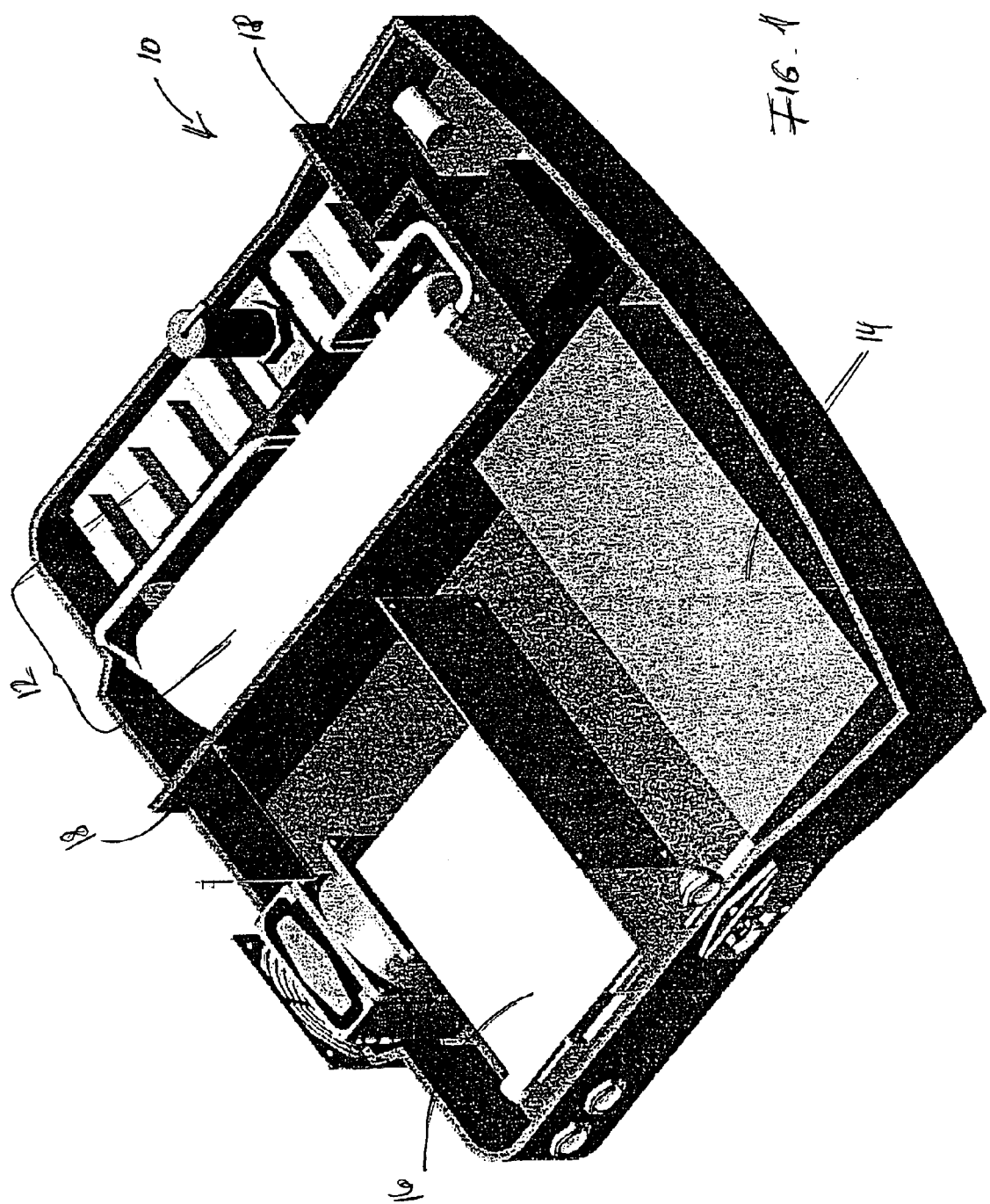

TEST DEVICE FOR FILTER SYSTEMS

BACKGROUND OF THE INVENTION

The present invention relates to a test device for filter systems. Test devices for filter systems, which comprise a pneumatic unit, a control unit, and a data processing unit, are known in the art. Such test devices are used, in particular, to test filter systems with membrane filters.

When testing membrane filters, it is important to keep the measurement conditions in the pneumatic unit, i.e., for instance, temperature, pressure, etc. as constant as possible. In prior art filter system test devices, however, the measurement conditions can frequently fluctuate, which leads to inaccurate measurement results.

SUMMARY OF THE INVENTION

It is an object of the invention to provide an improved test device for testing filter systems.

Another object of the invention is to provide a test device for filter systems that permits precise testing of filters.

These and other objects are achieved in accordance with the present invention as described and claimed hereinafter. In addition, further preferred aspects of the invention are also set out in the following description.

According to the invention, a test device for filter systems is provided, which test device comprises:

a pneumatic unit, a control unit for controlling the pneumatic unit, and a data processing unit, wherein the pneumatic unit is separated from the data processing unit and the control unit by a separating device substantially to shield the pneumatic unit against the heat generated in the data processing unit and the control unit.

By providing this separating device, the temperature in the pneumatic unit can be kept constant. As a result, the pressure in the pneumatic unit can be kept constant to enable very accurate measurement and testing of the filters to be measured.

The separating device is preferably comprises a heat insulating material, preferably a synthetic resin (plastic) with a relatively great wall thickness, foamed synthetic resin and/or a heat reflective coating. By providing a heat insulating material for the separating device, the pneumatic unit can be effectively shielded against the heat generated in the data processing unit and the control unit.

The devices of the data processing unit and/or the control unit that generate a lot of heat are preferably spaced at a large distance from the pneumatic unit. This further ensures that the temperature in the pneumatic unit remains substantially constant.

The pneumatic unit preferably comprises valves, pressure sensors, a valve block, and particularly preferably a reference tank.

The data processing unit preferably comprises an input interface, an output interface, a storage device, and a data and signal processing unit.

The control unit preferably comprises a device for controlling the compressed air being supplied to the pneumatic unit.

Other objects, features and advantages of the present invention will become evident from the following description.

BRIEF DESCRIPTION OF THE DRAWING

The invention will be described in further detail hereinafter with reference to an illustrative preferred embodiment shown in the accompanying drawing figure, which is a perspective view of a test device according to the present invention.

DETAILED DESCRIPTION OF PREFERRED EMBODIMENTS

The drawing figure shows a perspective view of a test device for filter systems according to a preferred embodiment of the invention. The inventive test device 10 comprises a pneumatic unit 12, a control unit 14, and a data processing unit 16.

The pneumatic unit 12 comprises an internal reference tank, and a plurality of valves and pressure sensors. The pneumatic unit 12 further comprises a compressed air supply and a connection to connect the filter to be tested.

The control unit 14 comprises a device for controlling the compressed air supplied to the pneumatic unit 12.

The data processing unit 16 comprises an input interface for inputting data and signals, an output interface for outputting data and signals, a storage device for storing data, and a data and signal processing device for processing data and signals. In the data and signal processing device, e.g., the test instructions entered into the test device are processed and forwarded to the control unit 14 described below. The storage device is used to store, for instance, test instructions and test results.

During the test cycle, the internal reference tank of the pneumatic unit 12 is filled with compressed air of a specific pressure. During a subsequent measurement, the reference tank is then used to determine the magnitude of the pressure drop in the filter and thus the quality of the filter.

The compressed air contained in the internal reference tank obeys the state equation of ideal gases in accordance with Boyle-Marriot, Gay-Lussac and Charles, which is:

$$\frac{p \cdot V}{T} = const. \tag{1}$$

If the temperature of the pneumatic unit 12, particularly of the reference tank, increases due to a temperature increase, the pressure in the internal reference tank changes. In particular, in accordance with the above equation (1), the pressure increases when the temperature increases because the volume of the reference tank is constant. The pressure in the reference tank increases by the same factor as that of the temperature increase. As a result, it is no longer possible precisely to determine the pressure drop and thus precisely to measure the performance of the filter. This increase in the temperature in the pneumatic unit 12 occurs largely because the devices of control unit 14 and/or data processing unit 16 heat up during operation.

For this reason, a separating device 18, which is preferably made of a heat insulating material, is provided in test device 10 according to the invention. The separating device 18 may be configured as a partition between pneumatic unit 12 and control unit 14 and data processing unit 16. Separating device 18 preferably partially surrounds pneumatic unit 12 such that the pneumatic unit 12 is shielded against the heat generated by control unit 14 and data processing unit 16. In such a case, separating device 18 comprises sidewalls, a cover section and a floor section. In a preferred embodiment, separating unit 18 is made of synthetic resin material with a relatively great wall thickness, foamed synthetic resin and/or a heat reflective coating.

Thus, at least two mutually sealed spaces can preferably be produced by separating device 18 to separate the temperature sensitive components, particularly the pneumatic unit, from the heat-generating components, particularly the control unit 14 and the data processing unit 16, of the test device 10 according to the invention.

In a preferred embodiment, the devices of data processing unit 16 and/or control unit 14 that generate a lot of heat are arranged as far as possible from the pneumatic unit 12, preferably diametrically opposite therefrom. As a result, pneumatic unit 12 is not only shielded against the heat generated by data processing unit 16 and/or control unit 14, but heating of pneumatic unit 12 is further reduced.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations falling within the scope of the appended claims and equivalents thereof.

What is claimed is:

1. A test device for filter systems, said device comprising:
    a pneumatic unit, the pneumatic unit comprising valves, pressure sensors, a valve block and a reference tank,
    a control unit for controlling the pneumatic unit, and
    a data processing unit,
    wherein the pneumatic unit is separated from the data processing unit and the control unit by a separating device which substantially shields the pneumatic unit against heat generated in the data processing unit and the control unit.

2. A test device according to claim 1, wherein the separating device comprises a heat insulating material.

3. A test device according to claim 2, wherein said heat insulating material is selected from the group consisting of plastics with a relatively great wall thickness, foamed plastics, and heat-reflective coatings.

4. A test device according to claim 1, wherein devices of the data processing unit and the control unit that generate substantial heat are spaced away from the pneumatic unit.

5. A test device according to claim 1, wherein the data processing unit comprises an input interface, an output interface, a storage device, and a data and signal processing device.

6. A test device according to claim 1, wherein the control unit comprises means for controlling the compressed air supplied to the pneumatic unit.

* * * * *

UNITED STATES PATENT AND TRADEMARK OFFICE
CERTIFICATE OF CORRECTION

PATENT NO. : 6,907,770 B2
DATED : October 26, 2004
INVENTOR(S) : Robert E. Wainwright, W. Michael Bissonnette and Richard J. Stoner II It is certified that error appears in the above-identified patent and that said Letters Patent is hereby corrected as shown below:

<u>Column 8,</u>
Line 15, please insert -- 1 -- between "claim" and "wherein".
Line 17, please insert -- 2 -- between "claim" and "wherein".

Signed and Sealed this

Twelfth Day of July, 2005

JON W. DUDAS
*Director of the United States Patent and Trademark Office*

UNITED STATES PATENT AND TRADEMARK OFFICE
CERTIFICATE OF CORRECTION

PATENT NO.      : 6,907,770 B2
DATED           : June 21, 2005
INVENTOR(S)     : Jochen Von Der Hardt et al.

It is certified that error appears in the above-identified patent and that said Letters Patent is hereby corrected as shown below:

This certificate supersedes certificate of correction issued July 12, 2005, the number was erroneously mentioned and should be vacated since no Certificate of Correction was granted.

Signed and Sealed this

First Day of November, 2005

JON W. DUDAS
*Director of the United States Patent and Trademark Office*